US00PP25922P2

(12) United States Plant Patent
Lannes

(10) Patent No.: US PP25,922 P2
(45) Date of Patent: Sep. 22, 2015

(54) ***MANDEVILLA* PLANT NAMED 'LANCOLORADO'**

(50) Latin Name: *Mandevilla hybrida*
Varietal Denomination: Lancolorado

(71) Applicant: Robert Lannes, Malause (FR)

(72) Inventor: Robert Lannes, Malause (FR)

(73) Assignee: D. H. M. Innovations S.A.S., Malause (FR)

( * ) Notice: Subject to any disclaimer, the term of this patent is extended or adjusted under 35 U.S.C. 154(b) by 75 days.

(21) Appl. No.: 13/998,543

(22) Filed: Nov. 8, 2013

(51) Int. Cl.
*A01H 5/02* (2006.01)

(52) U.S. Cl.
USPC ..... Plt./232

(58) Field of Classification Search
USPC ..... Plt./232
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'Lancolorado', characterized by its upright to trailing plant habit; moderately vigorous growth habit; moderately glossy dark green-colored leaves; freely flowering habit; and dark pink-colored flowers.

2 Drawing Sheets

Botanical designation: *Mandevilla hybrida.*
Cultivar denomination: 'LANCOLORADO'.

BACKGROUND OF THE INVENTION

The present invention relates to a new and distinct cultivar of *Mandevilla* plant, botanically known as *Mandevilla hybrida* and hereinafter referred to by the name 'Lancolorado'.

The new *Mandevilla* plant is a product of a planned breeding program conducted by the Inventor in Malause, France. The objective of the breeding program is to create new upright to trailing *Mandevilla* plants with numerous attractive flowers.

The new *Mandevilla* plant originated from a cross-pollination conducted by the Inventor in Malause, France in June, 2009 of *Mandevilla hybrida* 'Sunparapibra', disclosed in U.S. Plant Pat. No. 19,649, as the female, or seed parent with *Mandevilla hybrida* 'Sunmanderemi', disclosed in U.S. Plant Pat. No. 16,449, as the male, or pollen, parent. The new *Mandevilla* plant was discovered and selected by the Inventor as a single flowering plant from within the progeny of the stated cross-pollination in a controlled greenhouse environment in Malause, France in June, 2012.

Asexual reproduction of the new *Mandevilla* plant by cuttings in a controlled greenhouse environment in Malause, France, since December, 2012 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lancolorado'.

These characteristics in combination distinguish 'Lancolorado' as a new and distinct *Mandevilla* plant:

1. Upright to trailing plant habit.
2. Moderately vigorous growth habit.
3. Moderately glossy dark green-colored leaves.
4. Freely flowering habit.
5. Dark pink-colored flowers.

Plants of the new *Mandevilla* can be compared to plants of the female parent, 'Sunparapibra'. Plants of the new *Mandevilla* differ primarily from plants of 'Sunparapibra' in the following characteristics:

1. Plants of the new *Mandevilla* are more trialing than and not as upright as plants of 'Sunparapibra'.
2. Plants of the new *Mandevilla* have larger flowers than plants of 'Sunparapibra'.
3. Flowers of plants of the new *Mandevilla* are darker in color than flowers of plants of 'Sunparapibra'.

Plants of the new *Mandevilla* can be compared to plants of the male parent, 'Sunmanderemi'. Plants of the new *Mandevilla* differ primarily from plants of 'Sunmanderemi' in the following characteristics:

1. Plants of the new *Mandevilla* are more trialing than and not as upright as plants of 'Sunmanderemi'.
2. Plants of the new *Mandevilla* have larger leaves than plants of 'Sunmanderemi'.
3. Flowers of plants of the new *Mandevilla* are dark pink in color whereas flowers of plants of 'Sunmanderemi' are red in color.

Plants of the new *Mandevilla* can also be compared to plants of *Mandevilla sanderi* 'Lannevada', disclosed in U.S. Plant Pat. No. 24,122. In side-by-side comparisons conducted in Malause, France, plants of the new *Mandevilla* differed primarily from plants of 'Lannevada' in flower color as plants of 'Lannevada' have dark red-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lancolorado' grown in a container.

The photograph on the second sheet is a close-up view of a typical flower of 'Lancolorado'.

DETAILED BOTANICAL DESCRIPTION

The aforementioned photographs and following observations, measurements and values describe plants grown during the spring in 10.5-cm containers in polyethylene-covered greenhouse in Malause, France and under cultural practices typical of *Mandevilla* commercial production. During the production of the plants, day temperatures ranged from 15° C. to 26° C. and night temperatures ranged from 14° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Lancolorado'.

Parentage:

*Female, or seed, parent.*—*Mandevilla hybrida* 'Sunparapibra', disclosed in U.S. Plant Pat. No. 19,649.

*Male, or pollen, parent.*—*Mandevilla hybrida* 'Sunmanderemi', disclosed in U.S. Plant Pat. No. 16,449.

Propagation:

*Type.*—By vegetative cuttings.

*Time to initiate roots, summer.*—About two weeks at 23° C. to 30° C.

*Time to initiate roots, winter.*—About three weeks at 23° C. to 25° C.

*Time to produce a rooted young plant, summer.*—About five to six weeks at 23° C. to 30° C.

*Time to produce a rooted young plant, winter.*—About six to eight weeks at 23° C. to 25° C.

*Root description.*—Fibrous, fine; light yellowish white in color.

*Rooting habit.*—Freely branching; medium density.

Plant description:

*Plant and growth habit.*—Upright to trailing plant habit; broadly upright; moderately vigorous growth habit.

*Plant height.*—About 31.6 cm.

*Plant diameter* (*spread*).—About 36.9 cm.

*Lateral branch description.*—Branching habit: Freely branching habit with about six lateral branches developing per plant; pinching enhances lateral branch development. Length: About 21.8 cm. Diameter: About 2 mm. Internode length: About 3 cm. Strength: Strong. Texture: Smooth, glabrous; luster, moderately glossy. Color, developing: Close to 144B. Color, developed: Close to 199A to 199C.

Leaf description:

*Arrangement.*—Opposite, simple.

*Length.*—About 5.1 cm.

*Width.*—About 4.1 cm.

*Shape.*—Broadly ovate to broadly elliptic.

*Apex.*—Abruptly acute.

*Base.*—Truncate.

*Margin.*—Entire.

*Texture, upper and lower surfaces.*—Smooth, glabrous; luster, moderately glossy.

*Venation pattern.*—Pinnate, reticulate.

*Color.*—Developing leaves, upper surface: Close to N137A. Developing leaves, lower surface: Close to 146A. Full expanded leaves, upper surface: Darker than between 139A and 147A; venation, close to 137D. Fully expanded leaves, lower surface: More green than 146A; venation, close to 144C.

*Petiole length.*—About 9 mm.

*Petiole diameter.*—About 1.25 mm.

*Petiole texture, upper and lower surfaces.*—Smooth, glabrous.

*Petiole color, upper and lower surfaces.*—Close to 144A.

Flower description:

*Flower type and flowering habit.*—Single salverform flowers arranged in axillary cymes; flowers star-shaped and face mostly upright and outwardly; freely flowering habit with about five flowers developing per inflorescence and about 60 flowers developing per plant.

*Natural flowering season.*—Plants flower continuously from early summer into the autumn in France.

*Flower longevity on the plant.*—About seven days; flowers not persistent.

*Fragrance.*—Faint; sweet and pleasant.

*Inflorescence height.*—About 21 cm.

*Inflorescence diameter.*—About 14.8 cm.

*Flower buds.*—Length: About 6.2 cm. Diameter: About 9 mm. Shape: Narrowly obovate. Color: Close to 145B to 145C; towards the base, close to 144B; towards the apex, close to 53D.

*Flowers.*—Appearance: Flared trumpet, corolla fused and five-parted. Diameter: About 6.9 cm. Depth (length): About 7.5 cm. Tube length: About 6.1 cm.

*Corolla.*—Quantity and arrangement: Five petals arranged in a single whorl and fused toward the base. Petal length: About 9.6 cm. Petal width: About 2.9 cm. Petal shape and appearance: Roughly spatulate; lower 65% of the petal is fused. Petal apex: Non-symmetrically acute; slightly reflexed. Petal margin: Entire. Petal texture, upper surface: Smooth, glabrous; moderately velvety. Petal texture, lower surface: Smooth, glabrous; luster, slightly glossy. Throat and tube texture: Smooth, glabrous. Color: Petal, when opening, upper surface: Close to N57A to N57B; throat, close to between 12A and 13B; at the base of the throat, close to 145B. Petal, when opening, lower surface: Close to between 61C to 63B; main veins and towards the base of the non-fused part, close to 65C to 65D; tube, close to 145B to 145C; at the base of the tube, close to 145A tinged with close to 179B. Petal, fully opened, upper surface: Close to 58B; color does not change with development; throat, close to 15A; at the base of the throat, close to 145B. Petal, fully opened, lower surface: Close to 63B; main veins, close to 65C to 65D; tube, close to 58D and 150C to 150D; at the base of the tube, close to 145A tinged with close to 179B.

*Corona.*—Quantity and arrangement: Five sepals arranged in a single whorl. Sepal length: About 8 mm. Sepal width: About 2 mm. Sepal shape: Lanceolate. Sepal apex: Narrowly acuminate. Sepal base: Roughly truncate. Sepal margin: Entire. Sepal texture, upper and lower surfaces: Smooth, glabrous. Sepal color: Immature, upper and lower surfaces: Close to 144C. Mature, upper and lower surfaces: Close to 144C.

*Peduncles.*—Length: About 16 cm. Diameter: About 2.5 mm. Texture: Smooth, glabrous. Strength: Flexible, but strong. Color: Close to 144B.

*Pedicels.*—Length: About 2.2 cm. Diameter: About 2 mm. Texture: Smooth, glabrous. Strength: Flexible, but strong. Color: Close to 144A.

*Reproductive organs.*—Stamens: Quantity and arrangement: Typically five; basifixed; anthers connivent. Filament length: About 1 mm. Anther shape: Narrowly oblong. Anther length: About 1 cm. Anther color: Close to 161C. Pollen amount: None observed. Pistils: Quantity: Typically one. Pistil length: About 2.8 cm. Style length: About 2.5 cm. Style color: Close to 145A to 145B. Stigma shape: Sagittate. Stigma color: Close to 144C. Ovary color: Close to 144C.

*Seeds and fruits.*—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lancolorado' as illustrated and described.

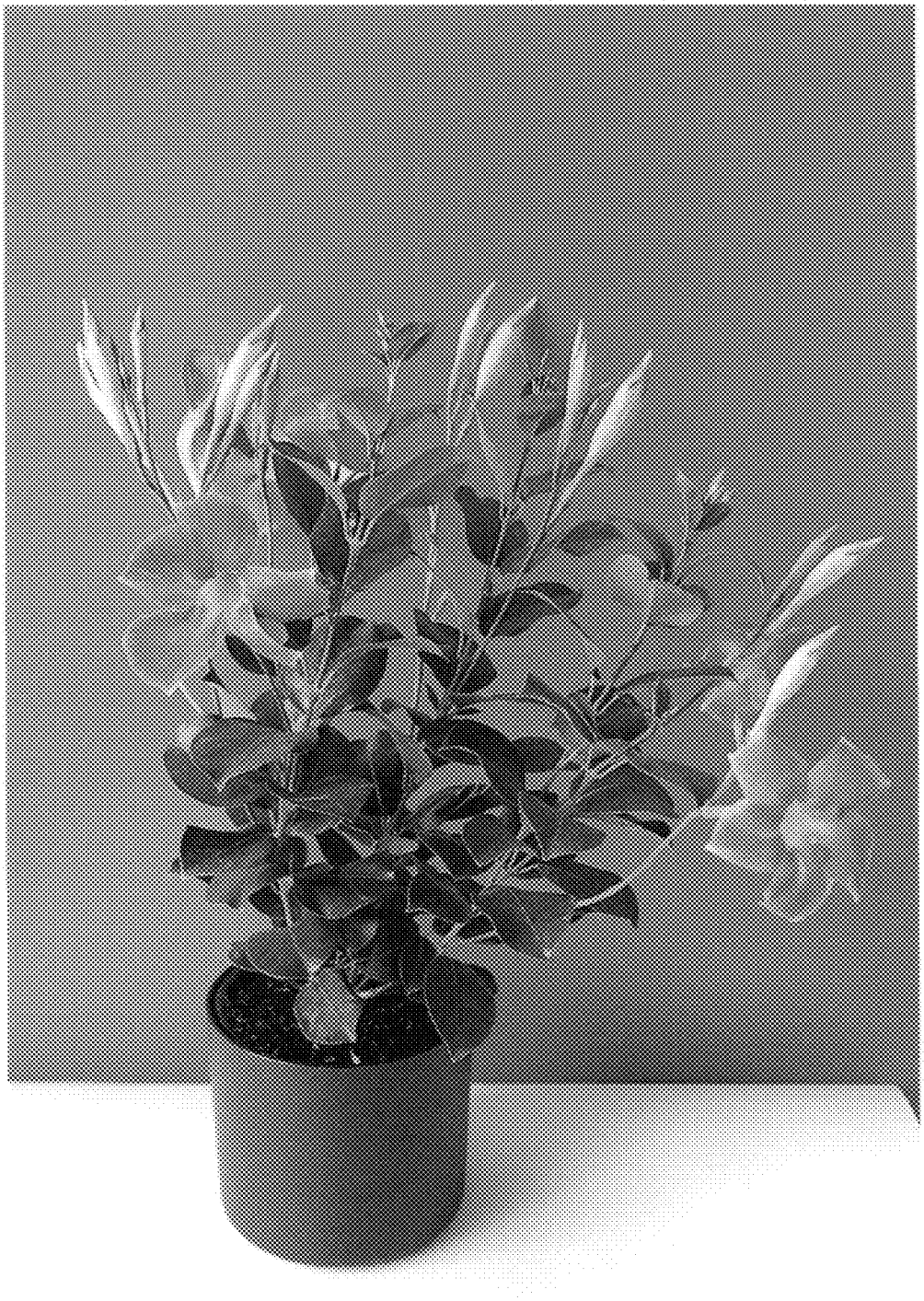

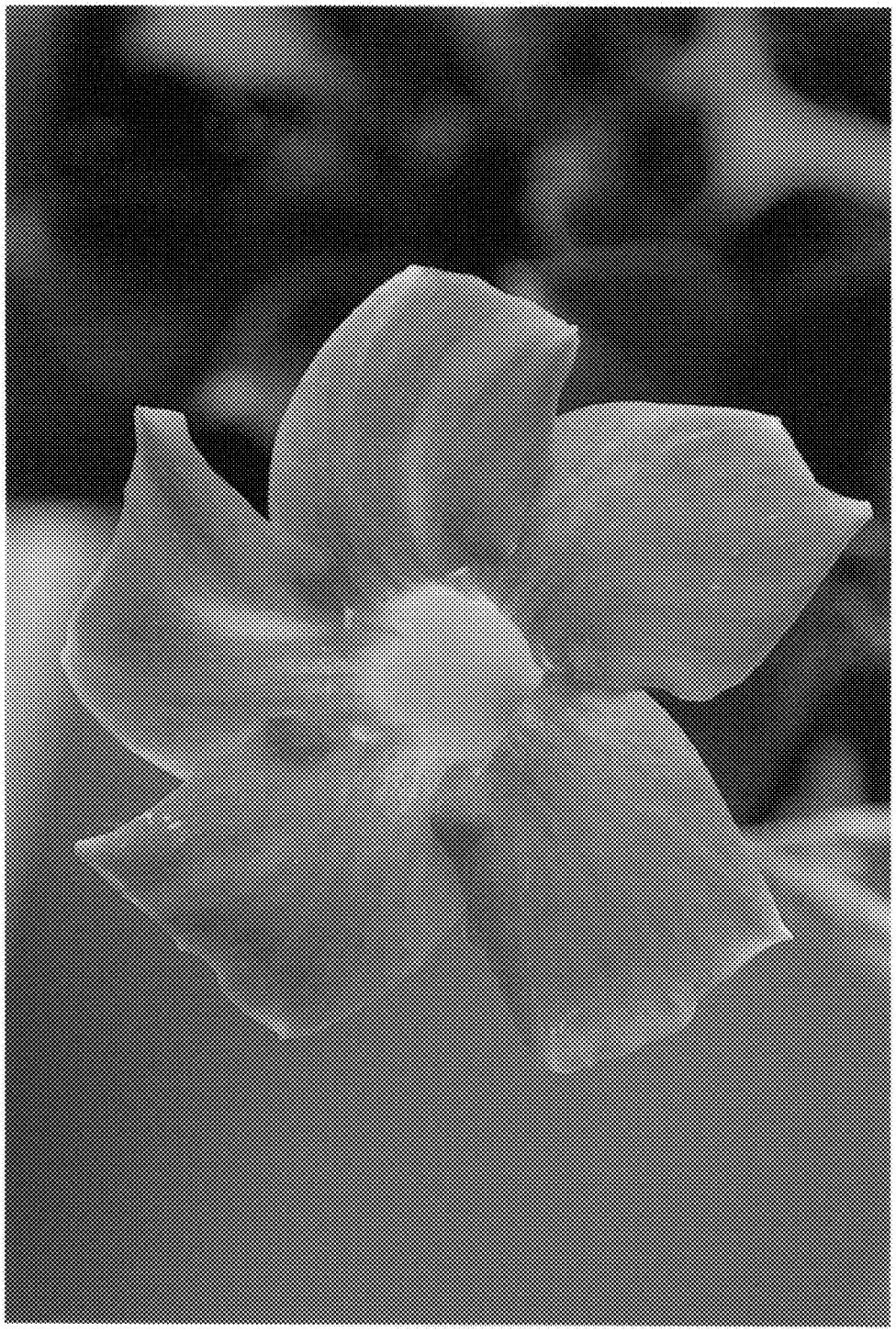

* * * * *